(12) United States Patent
Manning

(10) Patent No.: US 9,602,906 B1
(45) Date of Patent: Mar. 21, 2017

(54) EAR PLUGS FOR USE WHILE SLEEPING

(71) Applicant: Diaetta Heyward Manning, West Columbia, SC (US)

(72) Inventor: Diaetta Heyward Manning, West Columbia, SC (US)

( * ) Notice: Subject to any disclaimer, the term of this patent is extended or adjusted under 35 U.S.C. 154(b) by 0 days.

(21) Appl. No.: 14/704,152

(22) Filed: May 5, 2015

(51) Int. Cl.
| | | |
|---|---|---|
| *H04R 25/00* | (2006.01) | |
| *H04R 1/10* | (2006.01) | |
| *A61F 11/08* | (2006.01) | |
| *A61B 7/02* | (2006.01) | |

(52) U.S. Cl.
CPC ............ *H04R 1/1016* (2013.01); *A61F 11/08* (2013.01); *H04R 2225/021* (2013.01); *H04R 2225/63* (2013.01)

(58) Field of Classification Search
CPC   H04R 1/1016; H04R 1/105; H04R 2225/021; H04R 2225/63
USPC ................................. 381/328, 330, 380, 381
See application file for complete search history.

(56) References Cited

U.S. PATENT DOCUMENTS

| | | | |
|---|---|---|---|
| 968,008 A | 8/1910 | Waller | |
| 3,301,253 A | 1/1967 | Aram Glorig | |
| 4,552,137 A | 11/1985 | Strauss | |
| 5,046,580 A * | 9/1991 | Barton | H04R 25/656 128/866 |
| 5,224,495 A | 7/1993 | Robinson | |
| 6,041,440 A | 3/2000 | Jackson | |
| 6,123,168 A | 9/2000 | Berg | |
| D479,319 S | 9/2003 | Falco | |
| 7,512,414 B2 * | 3/2009 | Jannard | G02C 11/06 381/376 |
| 8,265,328 B2 * | 9/2012 | Milde | H04R 1/1066 381/370 |
| 2003/0002705 A1 * | 1/2003 | Boesen | H04M 1/6066 381/380 |
| 2005/0247515 A1 * | 11/2005 | Berg | H04R 1/1058 181/135 |
| 2006/0169291 A1 | 8/2006 | Shirai | |

* cited by examiner

*Primary Examiner* — Sunita Joshi

(57) ABSTRACT

The earplugs for use while sleeping are a set of earplugs adapted to suppress noise from reaching the eardrum of the user while remaining securely in place while sleeping. The earplugs for use while sleeping incorporate a timing device and a tone generating device that generates an alarm adapted to wake the wearer at a predetermined time. The earplugs for use while sleeping comprises a plurality of individual earplugs.

1 Claim, 6 Drawing Sheets

US 9,602,906 B1

EAR PLUGS FOR USE WHILE SLEEPING

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of earplugs, more specifically, a set of earplugs that are adapted for use while sleeping.

SUMMARY OF INVENTION

The earplugs for use while sleeping are a set of earplugs adapted to suppress noise from reaching the eardrum of the user while remaining securely in place while sleeping. The earplugs for use while sleeping incorporate a timing device and a tone generating device that generates an alarm adapted to wake the wearer at a predetermined time.

These together with additional objects, features and advantages of the earplugs for use while sleeping will be readily apparent to those of ordinary skill in the art upon reading the following detailed description of the presently preferred, but nonetheless illustrative, embodiments when taken in conjunction with the accompanying drawings.

In this respect, before explaining the current embodiments of the earplugs for use while sleeping in detail, it is to be understood that the earplugs for use while sleeping is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the earplugs for use while sleeping.

It is therefore important that the claims be regarded as including such equivalent construction insofar as they do not depart from the spirit and scope of the earplugs for use while sleeping. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
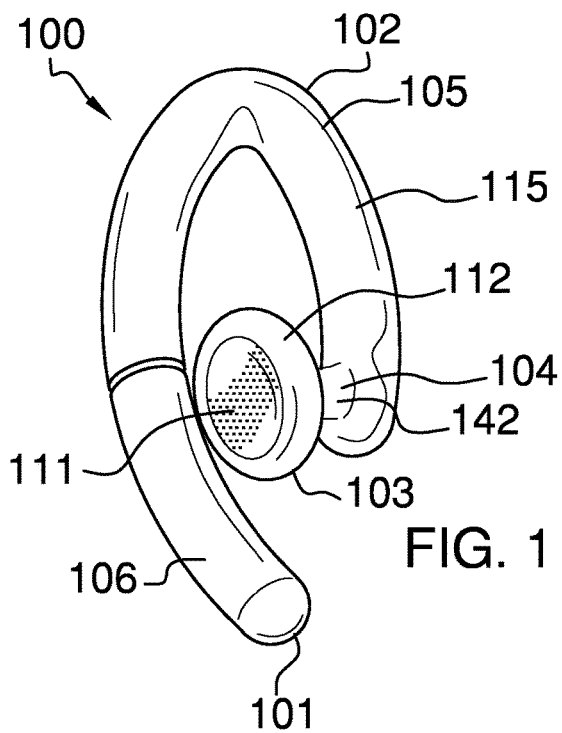
FIG. 1 is a perspective view of an embodiment of the disclosure.
Figure 2:
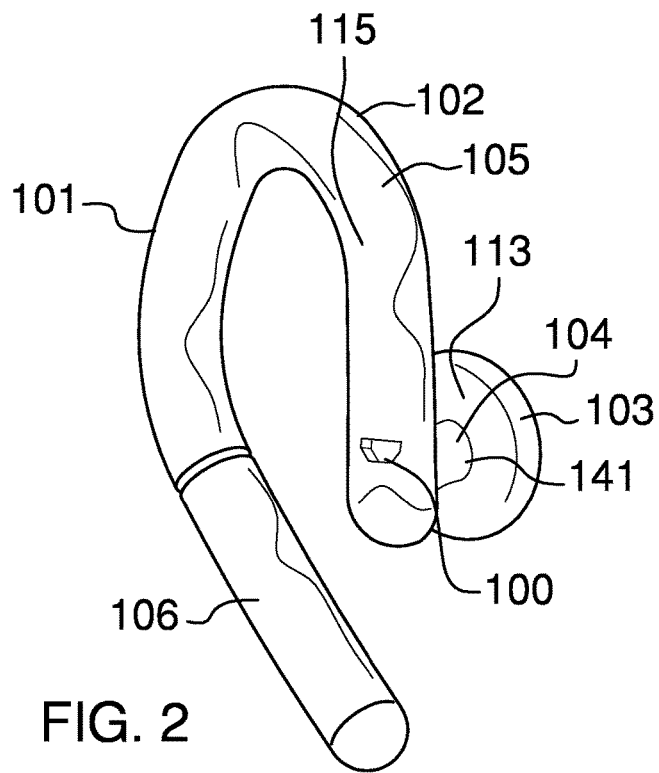
FIG. 2 is a back perspective view of an embodiment of the disclosure.
Figure 3:
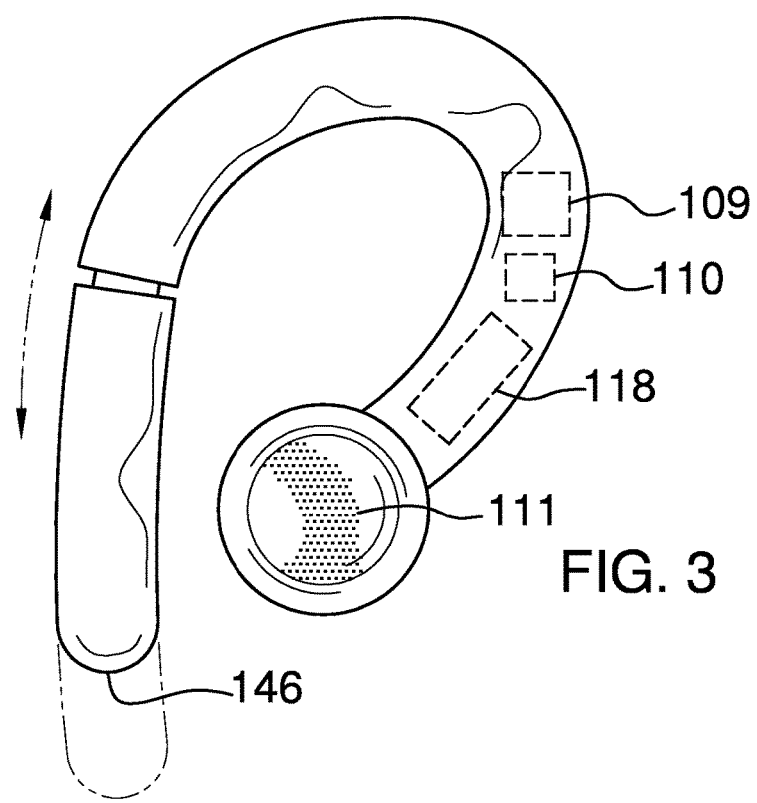
FIG. 3 is a front view of an embodiment of the disclosure.
Figure 4:
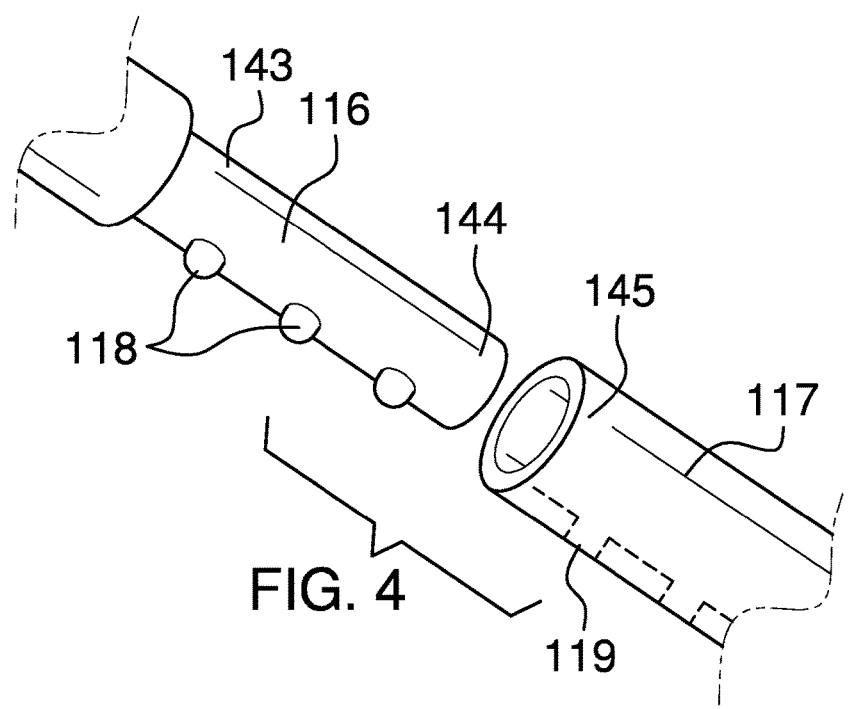
FIG. 4 is a detail view of an embodiment of the disclosure.
Figure 5:
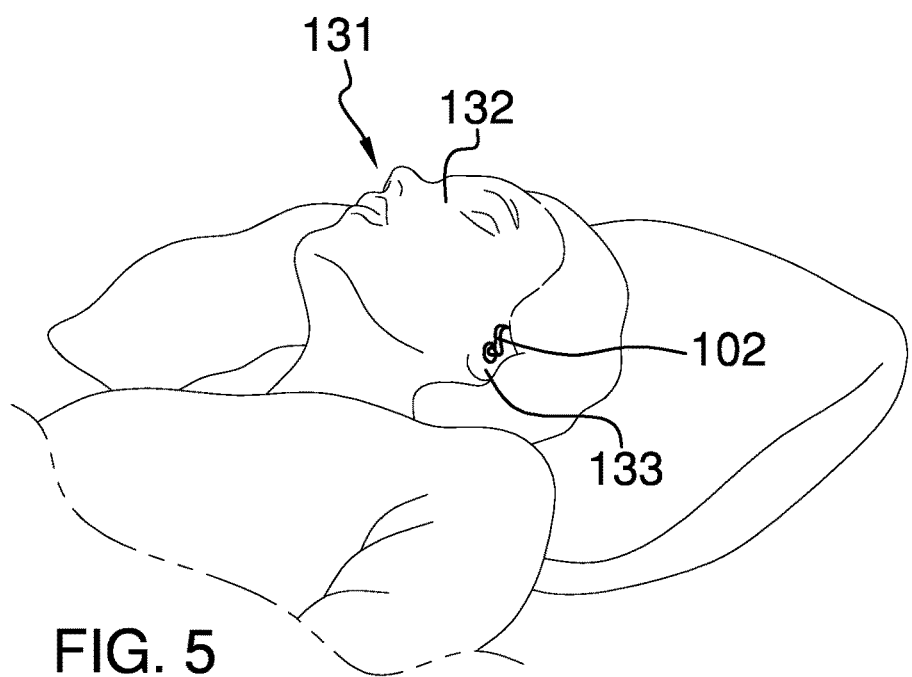
FIG. 5 is an in use view of an embodiment of the disclosure.
Figure 6:
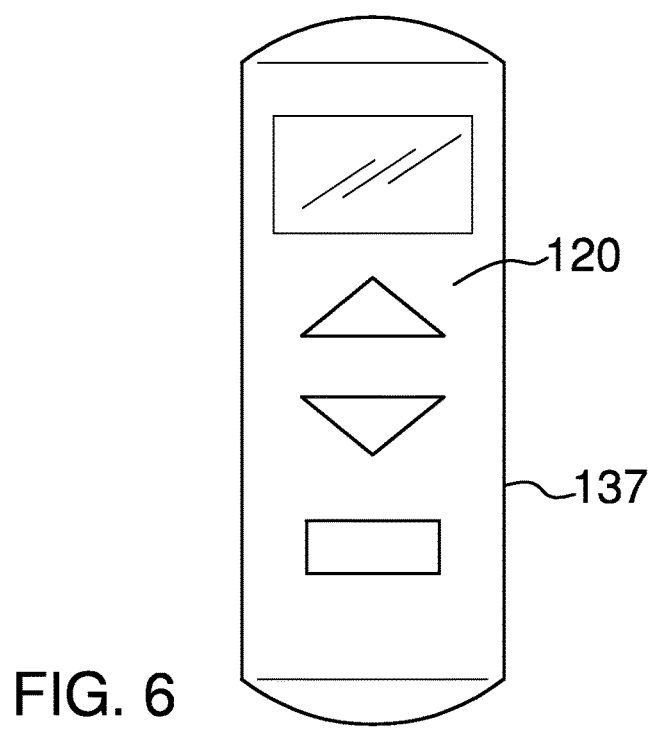
FIG. 6 is a detail view of an embodiment of the disclosure.
Figure 7:
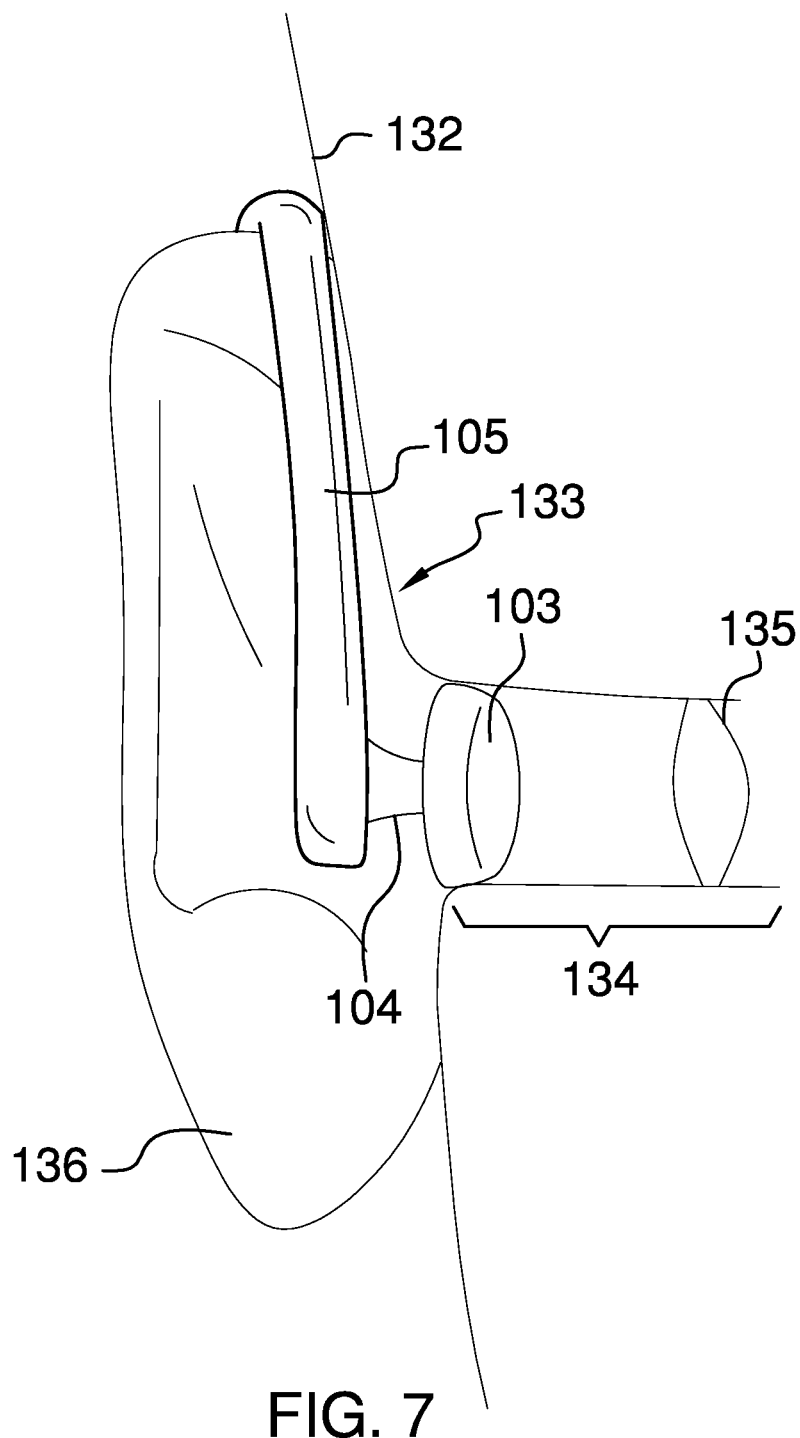
FIG. 7 is an in use view of an embodiment of the disclosure.
Figure 8:
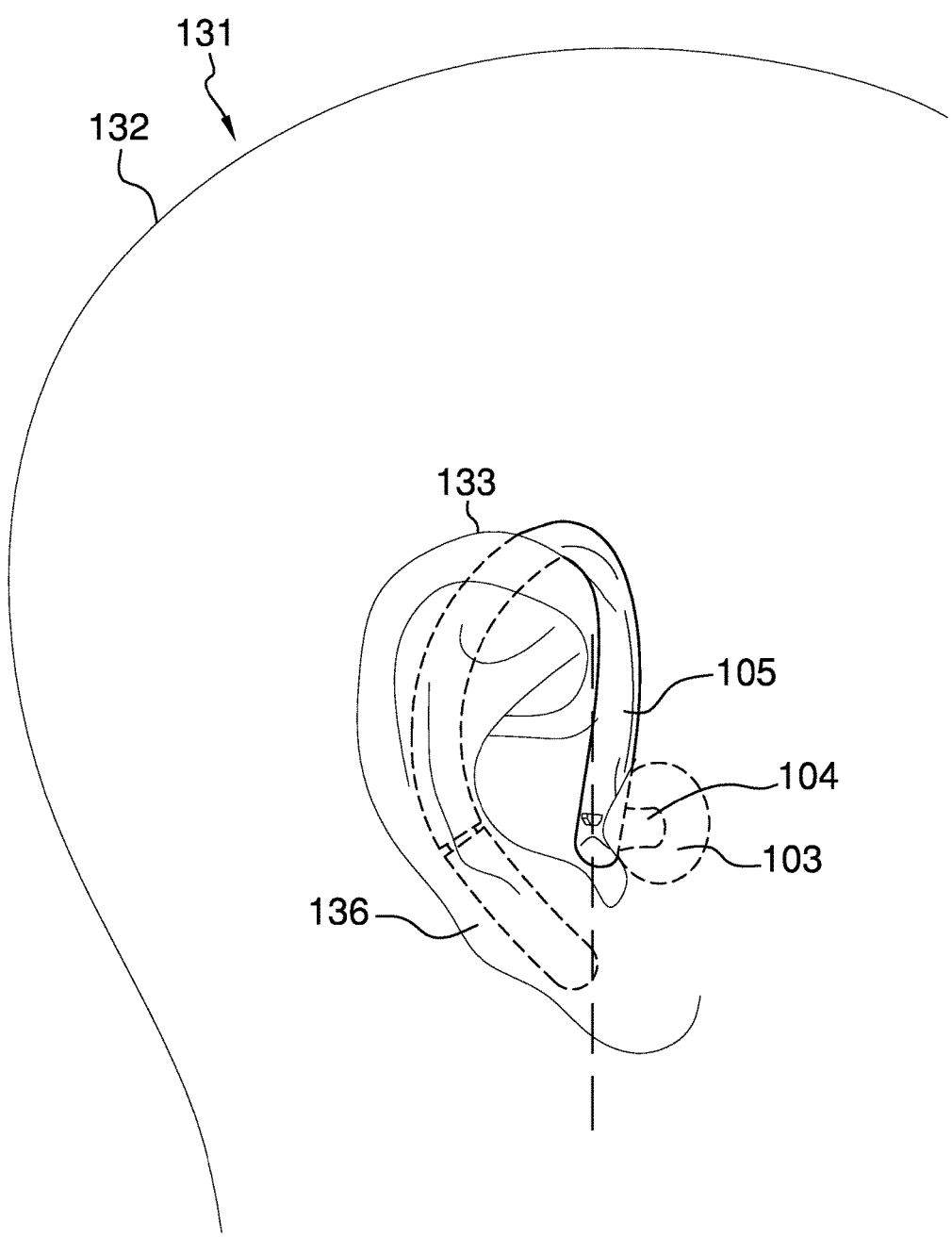
FIG. 8 is an in use view of an embodiment of the disclosure.
Figure 9:
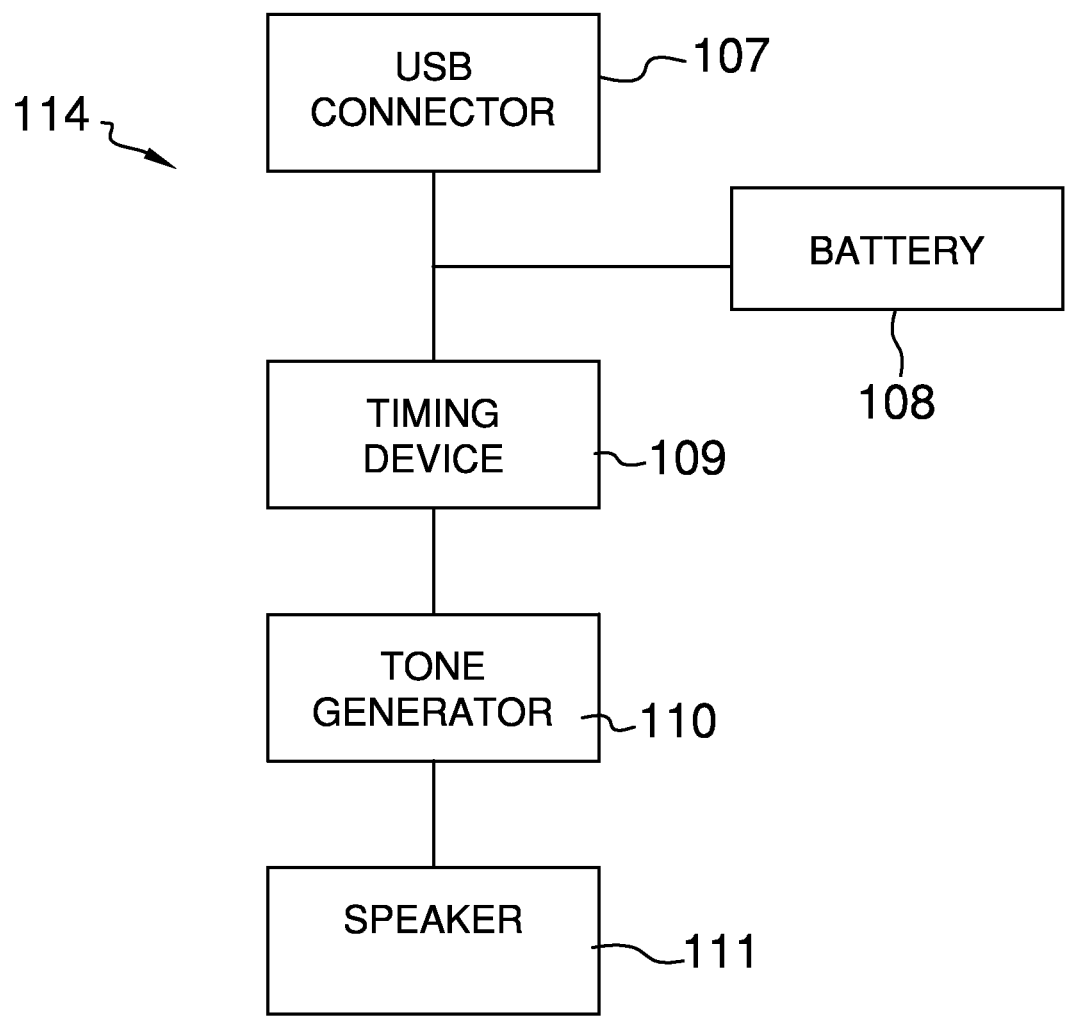
FIG. 9 is a block view of an embodiment of the disclosure.

Detailed reference will now be made to a first potential embodiment of the disclosure, which is illustrated in FIGS. 1 through 9.

The earplugs for use while sleeping 100 (hereinafter invention) comprises a plurality of individual earplugs 101. Each individual earplug 102 selected from the plurality of individual earplugs 101 further comprises a annular member 103, an earplug stem 104, a support member 105, and an extension 106.

The annular member 103 is a ring shaped structure that is adapted to fit inside the ear canal 134. The annular member 103 further comprises a speaker 111, a sound reducing memory foam 112, and a first housing 113. The speaker 111 is small enough to fit inside the ear canal 134 of the user 131. The purpose of the speaker 111 is discussed elsewhere in this disclosure. The first housing 113 is a casing that encloses the speaker 111 and the electrical connections to the speaker 111. The outer surface of the first housing 113 is ringed in a sound reducing memory foam 112 which can be, but is not limited to, a high density polyurethane foam. The sound reducing memory foam 112 is compressed to allow the annular member 103 to be inserted inside the ear canal 134. Once the sound reducing memory foam 112 is released, the foam expands back to its original shape which plugs the ear canal 134. The purpose of the annular member 103 is to prevent external noise from entering the ear canal 134. The speaker 111 and first housing 113 physically block the bulk of the external noise. The sound reducing memory foam 112 prevents the external noise from spilling around the speaker 111 and first housing 113 into the ear canal 134.

The earplug stem 104 is a small hollow post that is used to connect the annular member 103 to the support member 105. The earplug stem 104 is further defined with a first end 141 and a second end 142. The first end 141 of the earplug stem 104 is attached to the annular member 103. The second end 142 of the earplug stem 104 is attached to the support member 105. The hollow center of the earplug stem 104 allows for running wires from the support member 105 to the speaker 111.

The support member 105 further comprises a second housing 115 and an electronic system 114. The electronic system 114 further comprises a USB connection 107, a battery 108, a timing device 109, and a tone generating device 110. The second housing 115 is a casing that is adapted to fit around the user's 131 ear 133 in the space between the head 132 and the ear lobe 136. The electronic system 114 is contained within the second housing 115. The USB connection 107 is an electrical interface that can be: 1) used to recharge the battery 108; and, 2) adapted to permit communication between the invention 100 and an external electronic device 137 that can be used to adjust the operation of the electronic system 114. The battery 108 is a container consisting of one or more cells, in which chemical energy is converted into electricity and used as a source of electrical power for the invention 100. The timing device 109 is an electrical circuit that is used to activate or deactivate the tone generating device 110 after a predetermined amount of time. The tone generating device 110 is used to generate the electrical signal that the speaker 111 uses to create sounds audible the user 131.

In the first potential embodiment of the disclosure, the electronic system 114 is used as an alarm. In this scenario, the timing device 109 is set using the external electronic device 137 connected through the USB connection 107. Once the predetermined time has been reached, the timing device 109 activates the tone generating device 110 which generates a chirping noise that can be used to wake the user 131.

In the second potential embodiment of the disclosure, the electronic system 114 is used as a noise cancelling system. In this scenario, the timing device 109 is set and the tone generating device 110 is activated using the external electronic device 137 connected through the USB connection 107. The tone generating device 110 is used to generate a pattern of sounds that cancel out any external noise that may be leaking into the ear canal 134 to the ear drum 135. The tone generating device 110 continues to generate this pattern of sounds for a predetermined amount of time. Once the predetermined amount of time has been reached, the timing device 109 deactivates the tone generating device 110.

The extension 106 is a structure that is attached to the support member 105 at the end of the support member 105 distal from the earplug stem 104. The attachment of the extension 106 to the support member 105 is adjustable. By adjusting the attachment of the extension 106 to the support member 105, the fit of the invention 100 around the user's 131 ear 133 can be adjusted. The extension 106 further comprises a detent post 116 and a cover post 117. The detent post 116 is sized to fit within the cover post 117. The detent post 116 is fitted with a plurality of detents 118 which are a collection of spring operated balls that can be used to hold the cover post 117 in position. The cover post 117 is fitted with a detent hole 119 that is sized to receive each of the plurality of detents 118. The detent post 116 is further defined with a third end 143 and a fourth end 144. The cover post 117 is further defined with a fifth end 145 and a sixth end 146. The third end 143 of the detent post 116 is attached to the extension 106. The cover post 117 is hollow and is sized to fit over the detent post 116. The fifth end 145 of the cover post 117 slides over the fourth end 144 of the detent post 116 and is slid over the detent post 116 until the cover post 117 is in the appropriate position and one of the plurality of detents 118 catches the detent hole 119.

Generally, it is expected that the plurality of earplugs will comprise a seventh individual earplug 147 and an eighth individual earplug 148. To use the invention 100 the seventh individual earplug 147 is first connected to the external electronic device 137 to reset the timing device 109 and to activate or to deactivate the tone generating device 110. Next the eighth individual earplug 148 is connected to the external electronic device 137 to reset the timing device 109 and to activate or to deactivate the tone generating device 110. The user 131 then places the seventh individual earplug 147 and the eighth individual earplug 148 in both ears 133. When done using the invention 100, the seventh individual earplug 147 and the eighth individual earplug 148 are removed from the user's 131 ears 133. In a third potential embodiment of the disclosure, a remote control 120 is incorporated into the invention 100 to act as the external electronic device 137.

Speakers, batteries, USB connections, timing devices, and tone generating devices are commercially available and their use is well known and documented in the art. Sound reducing memory foams are well known and documented in the art. The remaining components can be made from molded plastics including, but not limited to, polycarbonate or polyethylene. Methods to incorporate remote controls into the operation of electronic devices are well known and documented in the art.

The following definitions were used in this disclosure:

Speaker: As used in this disclosure, the term a speaker is an electrical device that converts an electrical signal into an audible sound.

With respect to the above description, it is to be realized that the optimum dimensional relationship for the various components of the invention described above and in FIGS. 1 through 9, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

Is shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An earplug system comprising:
a plurality of individual earplugs;
wherein each individual earplug is adapted to fit in an ear canal;
wherein each individual earplug is adapted to fit around an ear in the space between a head and an ear lobe;
wherein each individual earplug incorporates a means to generate sound audible within the ear canal;
wherein each individual earplug is adapted for use while sleeping;
wherein each individual earplug selected from the plurality of individual earplugs further comprises an annular member, an earplug stem, a support member, and an extension;
wherein the annular member is a ring shaped structure that is adapted to fit inside the ear canal;

wherein the annular member further comprises a speaker, a sound reducing memory foam, and a first housing;

wherein the speaker is small enough to fit inside the ear canal;

wherein the outer surface of the first housing is ringed in a sound reducing memory foam;

wherein the earplug stem is a small hollow post that is used to connect the annular member to the support member;

wherein the support member further comprises a second housing and an electronic system;

wherein the electronic system further comprises a USB connection, a battery, a timing device, and a tone generating device;

wherein the second housing is a casing that is adapted to fit around the ear in the space between the head and the ear lobe;

wherein the electronic system is contained within the second housing;

wherein the annular member further comprises a speaker;

wherein the timing device is an electrical circuit that is used to activate or deactivate the tone generating device;

wherein an external electronic system is able to remotely communicate with the electronic system;

wherein the tone generating device is used to generate the electrical signal for the speaker;

wherein the electronic system is adapted to be an alarm device;

wherein the electronic system is adapted to be a noise cancelling device;

wherein the extension is a structure that is attached to the support member.

* * * * *